(12) United States Patent
Furcoiu

(10) Patent No.: US 11,187,366 B2
(45) Date of Patent: Nov. 30, 2021

(54) STENT FOR REPAIRING A PIPE

(71) Applicant: Mueller International, LLC, Atlanta, GA (US)

(72) Inventor: Aurelian Ioan Furcoiu, Chattanooga, TN (US)

(73) Assignee: Mueller International, LLC, Atlanta, GA (US)

( * ) Notice: Subject to any disclaimer, the term of this patent is extended or adjusted under 35 U.S.C. 154(b) by 0 days.

(21) Appl. No.: 16/786,246

(22) Filed: Feb. 10, 2020

(65) Prior Publication Data
US 2020/0292120 A1 Sep. 17, 2020

Related U.S. Application Data

(60) Provisional application No. 62/819,085, filed on Mar. 15, 2019.

(51) Int. Cl.
*F16L 55/163* (2006.01)

(52) U.S. Cl.
CPC .................................. *F16L 55/163* (2013.01)

(58) Field of Classification Search
CPC ..... F16L 55/16; F16L 55/163; F16L 55/1683; F16L 55/44; F16L 55/17
USPC .................. 138/98, 97; 405/150.1, 184.1
See application file for complete search history.

(56) References Cited

U.S. PATENT DOCUMENTS

| | | | |
|---|---|---|---|
| 3,895,652 A * | 7/1975 | Zach | B65D 39/12 |
| | | | 138/89 |
| 4,589,447 A * | 5/1986 | Kane | E03F 3/06 |
| | | | 138/98 |
| 4,647,072 A * | 3/1987 | Westman | B25B 27/02 |
| | | | 138/97 |
| 5,119,862 A | 6/1992 | Maimets et al. | |
| 5,351,720 A | 10/1994 | Maimets | |
| 6,712,556 B2 | 3/2004 | Penza | |
| 6,820,653 B1 | 11/2004 | Schempf et al. | |

(Continued)

FOREIGN PATENT DOCUMENTS

| | | |
|---|---|---|
| EP | 0621015 | 10/1994 |
| JP | 2005278993 | 10/2005 |

(Continued)

OTHER PUBLICATIONS

Braun, Clifton; International Preliminary Report on Patentability for PCT Application No. PCT/US18/63325, filed Nov. 30, 2018, dated Oct. 15, 2020, 7 pgs.

(Continued)

*Primary Examiner* — Patrick F Brinson
(74) *Attorney, Agent, or Firm* — Taylor English Duma LLP

(57) ABSTRACT

Example aspects of a stent spring for a stent, a stent for repairing a pipe, and a method for repairing a pipe are disclosed. The stent spring for a stent can comprise a plurality of minor springs connected in a series around a circumference of the stent spring, each of the minor springs defining a first leg and a second leg; and a spring constrictor engaged with each of the minor springs, each of the spring constrictors movable between a first position, wherein the corresponding minor spring defines a first maximum width, and a second position, wherein the corresponding minor spring defines a second maximum width that is greater than the first maximum width.

10 Claims, 5 Drawing Sheets

(56) References Cited

U.S. PATENT DOCUMENTS

| | | |
|---|---|---|
| 7,025,580 B2 | 4/2006 | Heagy et al. |
| 7,172,370 B2 | 2/2007 | Schmidt |
| 7,267,141 B1 | 9/2007 | De Meyer et al. |
| 8,488,290 B2 | 7/2013 | Kauffman |
| 8,783,297 B2 | 7/2014 | Hawwa et al. |
| 9,052,051 B2 | 6/2015 | Maimets et al. |
| 10,641,427 B2 | 5/2020 | Braun et al. |
| 11,079,058 B2 | 8/2021 | Furcoiu |
| 2002/0144822 A1 | 10/2002 | Hackworth et al. |
| 2003/0017775 A1 | 1/2003 | Sowinski et al. |
| 2003/0233140 A1 | 12/2003 | Hartley et al. |
| 2004/0236398 A1 | 11/2004 | Burgmeier et al. |
| 2008/0140178 A1 | 6/2008 | Rasmussen et al. |
| 2008/0255660 A1 | 10/2008 | Guyenot et al. |
| 2008/0269789 A1 | 10/2008 | Eli |
| 2010/0010617 A1 | 1/2010 | Goodson, IV et al. |
| 2010/0049313 A1 | 2/2010 | Alon et al. |
| 2011/0264186 A1 | 10/2011 | Berglung et al. |
| 2012/0273078 A1 | 11/2012 | Hawwa et al. |
| 2013/0018450 A1 | 1/2013 | Hunt |
| 2013/0131783 A1 | 5/2013 | Shalev et al. |
| 2013/0158646 A1 | 6/2013 | Roeder |
| 2016/0120638 A1 | 5/2016 | Michalak |
| 2016/0143732 A1 | 5/2016 | Glimsdale |
| 2016/0238178 A1 | 8/2016 | Urbanski |
| 2017/0231765 A1 | 8/2017 | Desrosiers et al. |
| 2017/0304092 A1 | 10/2017 | Hong et al. |
| 2019/0093813 A1 | 3/2019 | Badger et al. |
| 2019/0301657 A1 | 10/2019 | Braun et al. |
| 2020/0224811 A1 | 7/2020 | Braun et al. |
| 2020/0263823 A1 | 8/2020 | Furcoiu |
| 2020/0292119 A1 | 9/2020 | Furcoiu |
| 2020/0340610 A1 | 10/2020 | Furcoiu |
| 2021/0041051 A1 | 2/2021 | Furcoiu |
| 2021/0041052 A1 | 2/2021 | Furcoiu |

FOREIGN PATENT DOCUMENTS

| | | |
|---|---|---|
| KR | 1020070018627 | 2/2007 |
| WO | 2011001189 | 1/2011 |
| WO | 2019194870 | 10/2019 |
| WO | 2020172136 | 8/2020 |
| WO | 202019294 | 10/2020 |

OTHER PUBLICATIONS

Braun, Clifton; Non-Final Office Action for U.S. Appl. No. 16/112,207, filed Aug. 24, 2018, dated Nov. 5, 2019, 14 pgs.

Braun, Clifton; Notice of Allowance for U.S. Appl. No. 16/112,207, filed Aug. 24, 2018, filed Feb. 13, 2020, 13 pgs.

Braun, Clifton; International Search Report for PCT Application No. PCT/US18/63325, filed Nov. 30, 2018, dated Feb. 5, 2019, 8 pgs.

Furcoiu, Aurelian Ioan; International Search Report and Written Opinion for PCT Application No. PCT/US20/28038, Filed Apr. 14, 2020, dated Jun. 24, 2020, 9 pgs.

Furcoiu, Aurelian Ioan; International Search Report and Written Opinion for PCT Application No. PCT/US20/18593, Filed Feb. 18, 2020, dated May 7, 2020, 9 pgs.

Furcoiu, Aurelian Ioan; Requirement for Restriction/Election for U.S. Appl. No. 17/792,984, filed Feb. 18, 2020, dated Apr. 1, 2021, 6 pgs.

Furcoiu, Aurelian Ioan; Non-Final Office Action for U.S. Appl. No. 16/786,193, filed Feb. 10, 2020, dated Feb. 4, 2021, 22 pgs.

Braun, Clifton; Non-Final Office Action for U.S. Appl. No. 16/836,468, filed Mar. 31, 2020, dated May 20, 2021, 29 pgs.

Furcoiu, Aurelian Ioan; Examiner-Initiated Interview Summary for U.S. Appl. No. 16/845,557, filed Apr. 10, 2020, dated Apr. 21, 2021, 2 pgs.

Furcoiu, Aurelian Ioan; Non-Final Office Action for U.S. Appl. No. 16/792,984, filed Feb. 18, 2020, dated May 25, 2021, 25 pgs.

Furcoiu, Aurelian Ioan; Corrected Notice of Allowance for U.S. Appl. No. 16/786,193, filed Feb. 10, 2020, dated May 17, 2021, 6 pgs.

Furcoiu, Aurelian Ioan; Corrected Notice of Allowance for U.S. Appl. No. 16/786,193, filed Feb. 10, 2020, dated Jun. 22, 2021, 6 pgs.

Furcoiu, Aurelian Ioan; Notice of Allowance for U.S. Appl. No. 16/786,193, filed Feb. 10, 2020, dated Apr. 26, 2021, 9 pgs.

Braun, Clifton; Notice of Allowance for U.S. Appl. No. 16/836,468, filed Mar. 31, 2020, dated Aug. 12, 2021, 13 pgs.

Furcoiu, Aurelian Ioan; Non-Final Office Action for U.S. Appl. No. 16/845,557, filed Apr. 10, 2020, dated Aug. 17, 2021, 35 pgs.

Braun, Clifton; Corrected Notice of Allowance for U.S. Appl. No. 16/836,468, filed Mar. 31, 2020, dated Aug. 31, 2021, 6 pgs.

Braun, Cliff; Extended European Search report for application No. 18913510.6, filed Nov. 30, 2018, dated Sep. 13, 2021, 7 pgs.

Furcoiu, Aurelian Ioan; International Preliminary Report on Patentability for PCT Application No. PCT/US20/18593, filed Feb. 18, 2020, dated Sep. 2, 2021.

* cited by examiner

STENT FOR REPAIRING A PIPE

CROSS-REFERENCE TO RELATED APPLICATIONS

The present application claims the benefit of U.S. Provisional Application No. 62/819,085, filed Mar. 15, 2019, which is hereby specifically incorporated by reference herein in its entirety.

TECHNICAL FIELD

This disclosure relates to pipe repair. More specifically, this disclosure relates to a stent for repairing a damaged pipe.

BACKGROUND

Piping systems, including municipal water systems, can develop breaks in pipe walls that can cause leaking. Example of breaks in a pipe wall can include radial cracks, axial cracks, point crack, etc. Repairing a break in a pipe wall often requires the piping system to be shut off, which can be inconvenient for customers and costly for providers. Further, repairs can necessitate grandiose construction, including the digging up of streets, sidewalks, and the like, which can be costly and time-consuming.

SUMMARY

It is to be understood that this summary is not an extensive overview of the disclosure. This summary is exemplary and not restrictive, and it is intended neither to identify key or critical elements of the disclosure nor delineate the scope thereof. The sole purpose of this summary is to explain and exemplify certain concepts off the disclosure as an introduction to the following complete and extensive detailed description.

Disclosed is a stent spring for a stent comprising a plurality of minor springs connected in a series around a circumference of the stent spring, each of the minor springs defining a first leg and a second leg; and a spring constrictor engaged with each of the minor springs, each of the spring constrictors movable between a first position, wherein the corresponding minor spring defines a first maximum width, and a second position, wherein the corresponding minor spring defines a second maximum width that is greater than the first maximum width.

Also disclosed is a stent for repairing a pipe, the stent comprising a stent spring comprising a plurality of minor springs connected in a series; a spring constrictor engaged with each of the minor springs, each of the spring constrictors movable between a first position, wherein the stent is in a compressed configuration, and a second position, wherein the stent is in an expanded configuration; and a seal configured to engage an inner wall of a pipe.

A method for repairing a pipe is also disclosed, the method comprising providing a stent comprising a stent spring and a seal, the stent spring comprising a plurality of minor springs; orienting the minor springs in a constricted configuration to reduce a diameter of the stent; inserting the stent into a pipe; orienting the minor springs in an un-constricted configuration to increase the diameter of the stent; and engaging an inner wall of the pipe with the seal.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures may be designated by matching reference characters for the sake of consistency and clarity.

DETAILED DESCRIPTION

Figure 1:
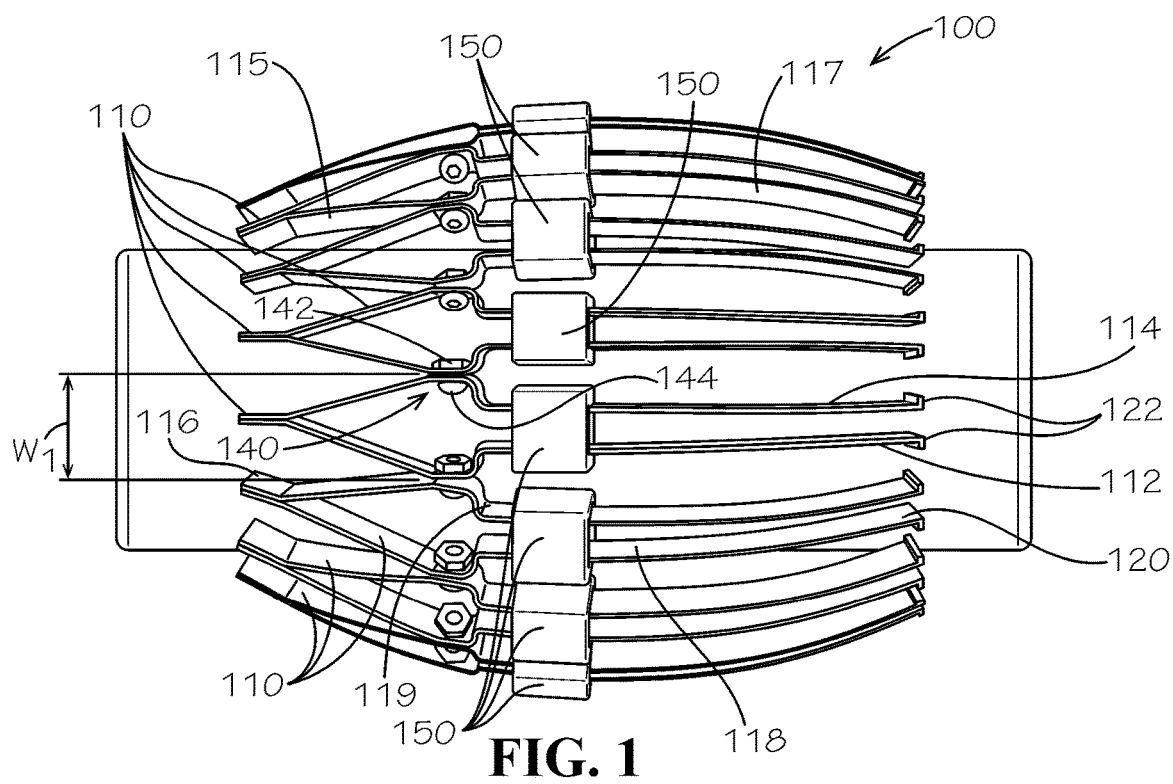
FIG. 1 is a side view of a stent spring, in accordance with one aspect of the present disclosure, the stent spring comprising a plurality of minor springs, each in a constricted configuration.

The present disclosure can be understood more readily by reference to the following detailed description, examples, drawings, and claims, and the previous and following description. However, before the present devices, systems, and/or methods are disclosed and described, it is to be understood that this disclosure is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description is provided as an enabling teaching of the present devices, systems, and/or methods in its best, currently known aspect. To this end, those skilled in the relevant art will recognize and appreciate that many changes can be made to the various aspects of the present devices, systems, and/or methods described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

As used throughout, the singular forms "a," "an" and "the" include plural referents unless the context clearly dictates otherwise. Thus, for example, reference to "an element" can include two or more such elements unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

For purposes of the current disclosure, a material property or dimension measuring about X or substantially X on a particular measurement scale measures within a range between X plus an industry-standard upper tolerance for the specified measurement and X minus an industry-standard lower tolerance for the specified measurement. Because tolerances can vary between different materials, processes and between different models, the tolerance for a particular measurement of a particular component can fall within a range of tolerances.

As used herein, the terms "optional" or "optionally" mean that the subsequently described event or circumstance can or cannot occur, and that the description includes instances where said event or circumstance occurs and instances where it does not.

The word "or" as used herein means any one member of a particular list and also includes any combination of members of that list. Further, one should note that conditional language, such as, among others, "can," "could," "might," or "may," unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily include logic for deciding, with or without user input or prompting, whether these features, elements and/or steps are included or are to be performed in any particular aspect.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutations of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific aspect or combination of aspects of the disclosed methods.

Disclosed in the present application is a stent for repairing a pipe and associated methods, systems, devices, and various apparatus. Example aspects of the stent can comprise a seal and a plurality of minor springs. The minor springs can be connected together to form a stent spring. It would be understood by one of skill in the art that the disclosed stent for repairing a pipe is described in but a few exemplary aspects among many. No particular terminology or description should be considered limiting on the disclosure or the scope of any claims issuing therefrom.

Figure 2:
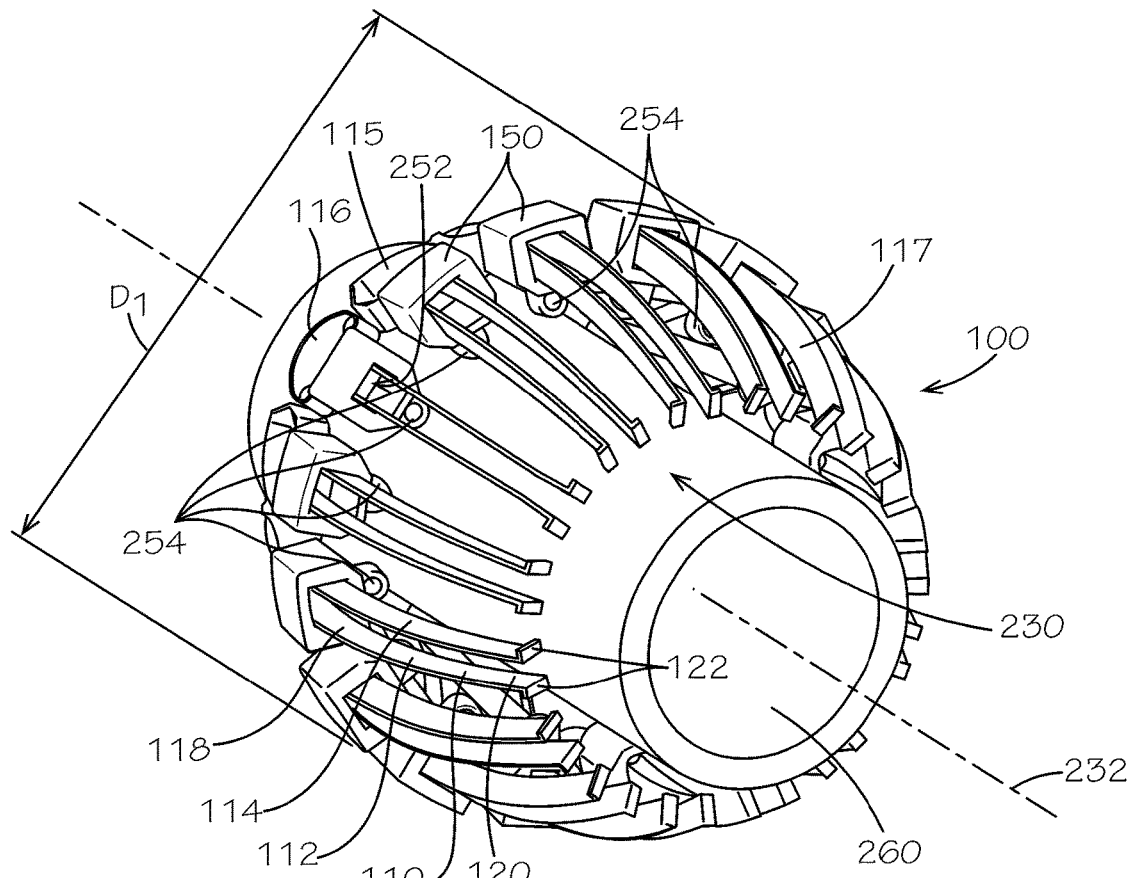
FIG. 2 is a top perspective view of the stent spring of FIG. 1.

FIGS. 1-2 illustrate a first aspect of a stent spring 100 for a stent 300 (shown in FIG. 3) according to the present disclosure. Referring to FIG. 1, as shown, the stent spring 100 can define a substantially cylindrical shape and a substantially circular cross-sectional shape. In the present aspect, the stent spring 100 can bow outward at or near a center thereof, such that a diameter of the stent spring 100 can vary along its length. Other aspects of the stent spring 100 may not bow outward as shown. Example aspects of the stent spring 100 can comprise a plurality of minor springs 110 connected together in a side-by-side series generally around the circumference of the stent spring 100. Each of the minor springs 110 can be connected to the adjacent minor springs 110 by a fastener 140. In the present aspect, each of the fasteners 140 can comprise a bolt 142 and a nut 144, as illustrated. Other aspects of the fasteners 140 can be clips, screws, adhesives, welding, or any other suitable fastener known in the art. Each of the minor springs 110 can generally define a first end 116, a second end 120 opposite the first end 116, and a middle section 118 therebetween. Furthermore, each of the minor springs 110 can comprise a first leg 112 and a second leg 114, and each of the first and second legs 112,114 can extend from the first end 116 to the second end 120. Each pair of first and second legs 112,114 can be joined together at the first end 116 of the minor spring 110 and can be spaced apart at the middle section 118 of the minor spring 110 and at the second end 120 of the minor spring 110. The first and second legs 112,114 can be joined at the first end 116 by welding in one example aspect. In other aspects, the first and second legs 112,114 can be joined together at the first end 116 by an adhesive, clip, screw, nut and bolt assembly, or any other suitable fastener.

According to example aspects, each of the minor springs 110 can joined to an adjacent one of the minor springs 110 by the fastener 140 at the middle sections 118 thereof. For example, the fastener 140 can couple the middle section 118 of the first leg 112 of a first one of the minor springs 110 to the middle section 118 of the second leg 114 of an adjacent minor spring 110, and so on. In some aspects, as shown, each of the fasteners 140 can be oriented along the middle sections 118 of the corresponding adjacent minor springs 110 at a position that can be closer to the first ends 116 of the minor springs 110 than the second ends 120. In other aspects, however, the fasteners 140 can be positioned at any suitable location along the minor springs 110. In various example aspects, each of the first and second legs 112,114 can generally define a head portion 115 and a tail portion 117, and the fastener 140 can be positioned at or near a joint 119 between the head portion 115 and the tail portion 117. For example, in the present aspect, the fastener 140 can be positioned on the head portion 115 adjacent to the joint 119. In the present aspect, the joint 119 can define a substantially S-shaped bend; however, in other aspects, the joint between the head and tail portions 115,117 can define any other suitable shape. In some aspects, as shown, a foot 122 can be formed on each of the first and second legs 112,114 at the second end 120 of the minor spring 110. In the present aspect, each of the feet 122 can extend away from the minor spring 110 at approximately a ninety-degree angle with respect to the corresponding first or second leg 112,114. Other aspects of the feet 122 can be oriented at any suitable angle relative to the corresponding first and second legs 112,114.

In some aspects, the minor springs 110 of the stent spring 100 can comprise a metal material, such as, for example, stainless steel, spring steel, aluminum, nitinol, or cobalt chromium. For example, in some aspects, the minor springs 110 can comprise flat strips of metal bent to form each of the minor springs 110. In other aspects, the minor springs 110 can comprise a plastic material, such as, for example, nylon, POM (polyoxymethylene), or PVC (polyvinyl chloride), and in still other aspects, the minor springs 110 can comprise a carbon fiber material, or any other suitable material known in the art. Optionally, the material of the minor springs 110 can be an NSF certified material that can comply with various public health safety standards. For example, in some aspects, the material can be approved as safe for use in drinking-water applications. Moreover, in some aspects, the minor springs 110 can comprise a coating, such as, for example, a rubber or liquid metal coating. The coating can improve mechanical properties of the stent spring 100 in some aspects. For example, the coating can improve the tensile strength of the stent spring 100 by providing a flexible and/or springy outer layer. In some aspects, the coating can also be corrosion resistant, or a separate coating can be applied to the stent spring 100 for corrosion resistance. For example, a corrosion resistant coating can comprise a zinc-nickel material, phosphate, electrophoretic paint (e-coating), polyester, fusion-bonded epoxy (FBE), or any other suitable corrosion resistant material.

Figure 3:
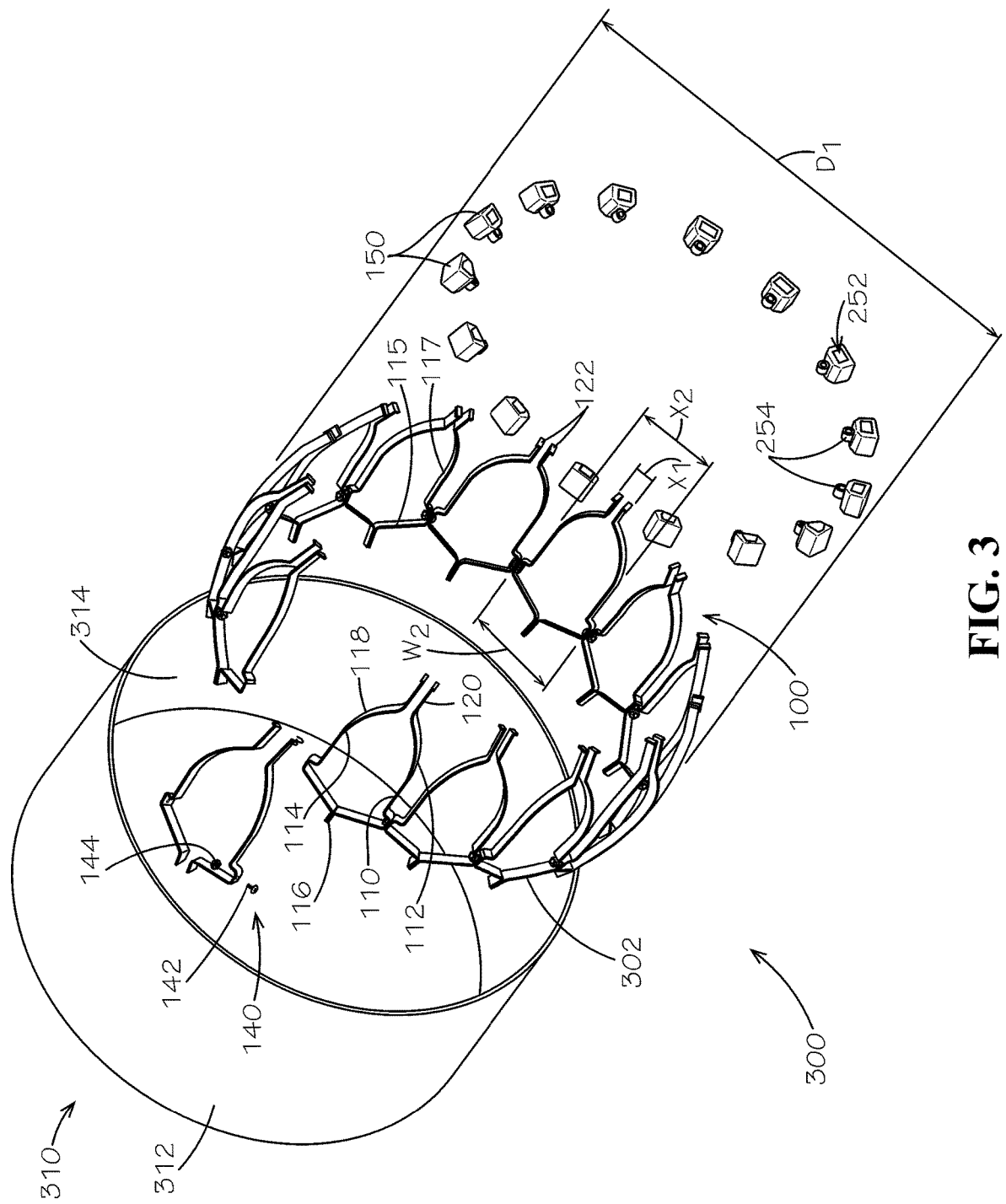
FIG. 3 is an exploded view of a stent according to an aspect of the present disclosure, wherein the stent comprises the stent spring of FIG. 1 and a seal, and wherein the minor springs of the stent spring are in an un-constricted configuration.
Figure 5:
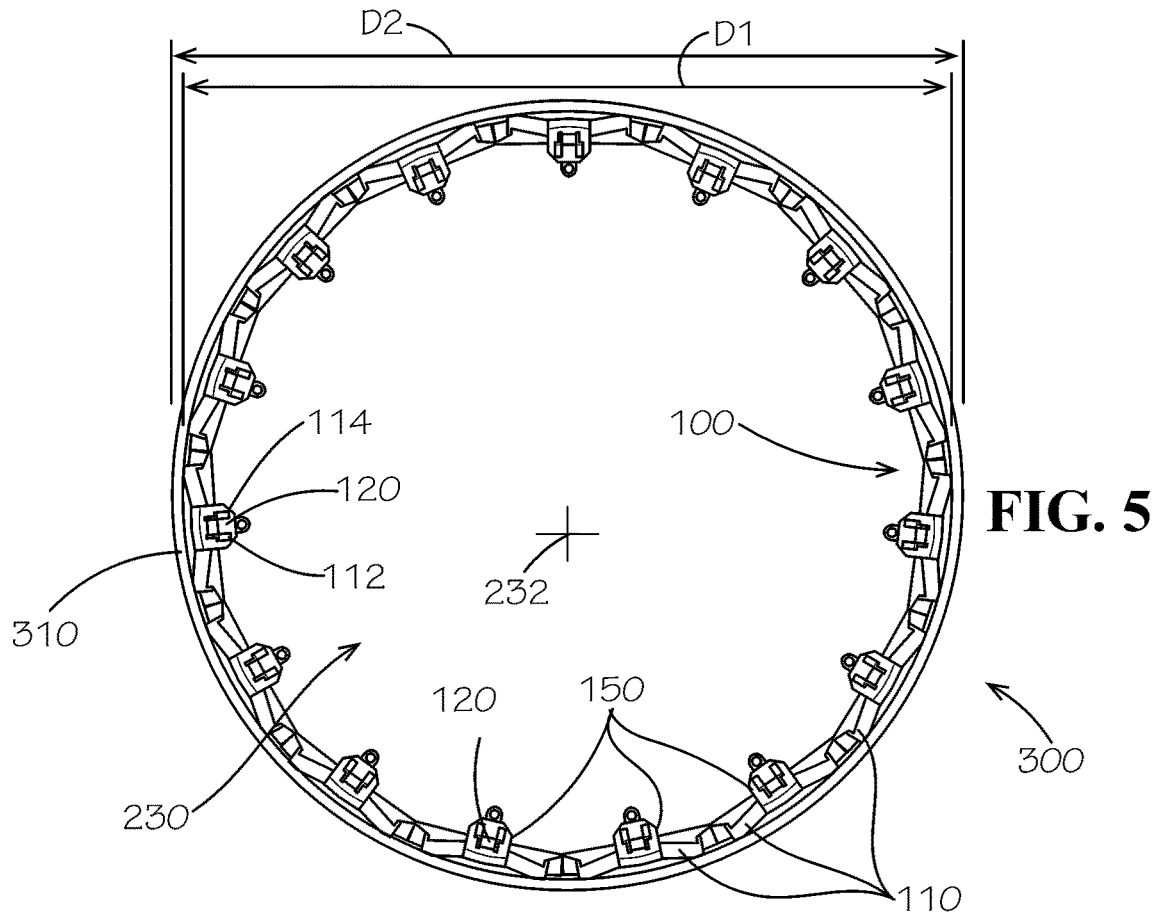
FIG. 5 is a front view of the stent of FIG. 3 in an expanded configuration.
Figure 6:
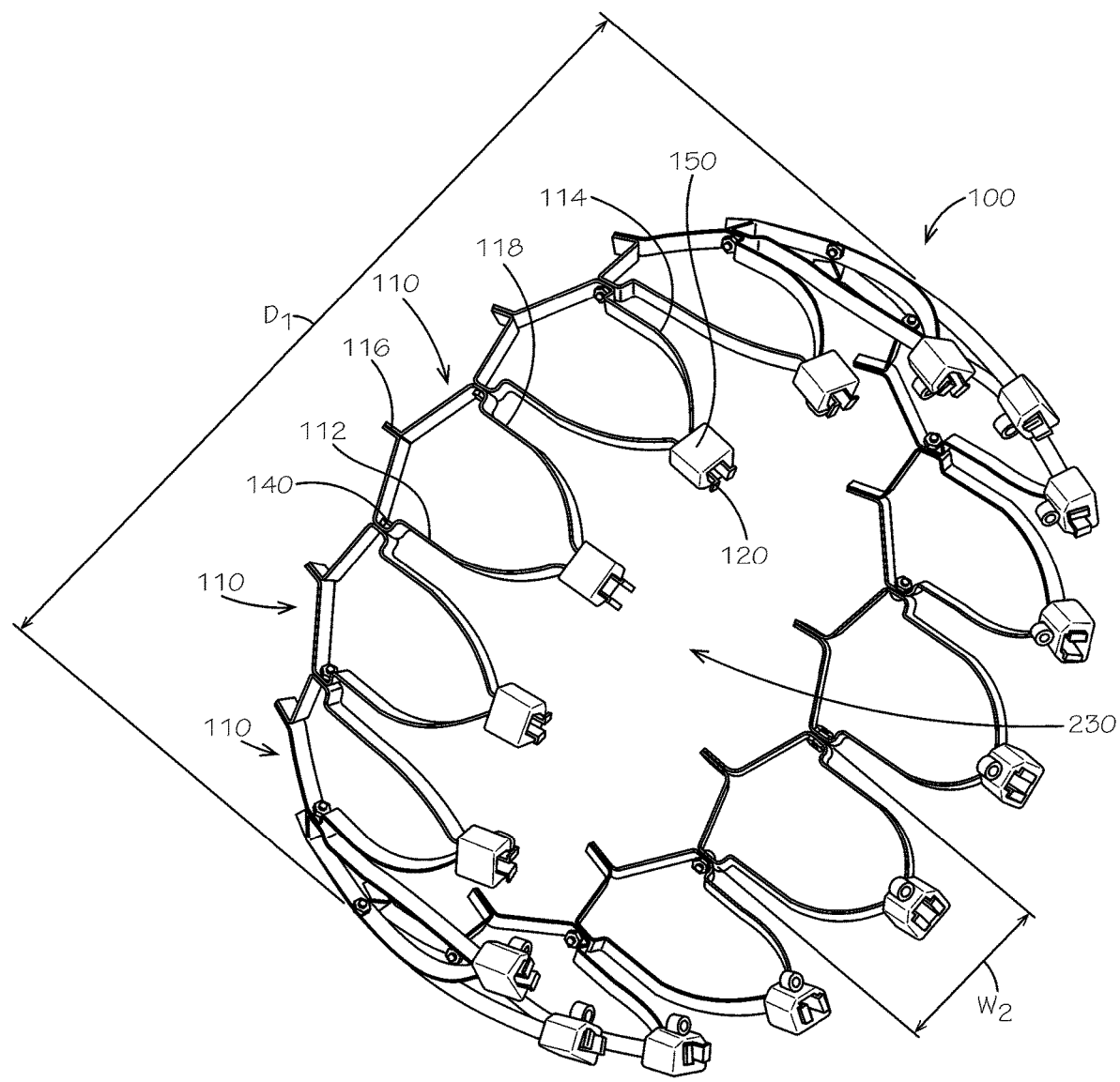
FIG. 6 is a top perspective view of the stent spring of FIG. 1, wherein the minor springs are in the un-constricted configuration.

According to example aspects, each of the minor springs 110 can define a spring force and can be expandable, such that the minor spring 110 can be oriented in a natural, un-constricted configuration, as shown in FIG. 3, and compressible, such that the minor springs 110 can be oriented in a constricted configuration, as shown in FIGS. 1 and 2. In example aspects, a spring constrictor 150 can be mounted on each of the minor springs 110, as shown, to bias the corresponding minor spring 110 to the constricted configuration. Example aspects of the spring constrictors 150 can be configured to engage the corresponding minor spring 110 by sliding on the middle section 118 of the corresponding minor spring 110, and more specifically, the spring constrictor 150 may be configured to slide on the tail portions 117 of the first and second legs 112,114. The spring constrictors 150 can be movable between a first position and a second position along the corresponding minor springs 110. In the first position, each spring constrictor 150 can be substantially centered on the middle section 118 of the minor spring 110, as shown in FIGS. 1, 2, 4, and 7. Furthermore, in some aspects, as shown, the spring constrictor can be mounted on the tail portions 117 of the first and second legs 112,114 and can be oriented proximate to the joints 119 between the corresponding head and tail portions 115,117. In the second position, the spring constrictor 150 can slide along the first and second legs 112,114 to a location proximate to the second end 120 of the minor spring 110, as shown in FIGS. 5, 6, and 8.

In the first position, the minor springs 110 can be in the constricted configuration wherein the first and second legs 112,114 can be biased towards one another by the spring constrictor 150 at the middle section 118 of the minor spring 110. As shown, in the constricted configuration, the first and second legs 112,114 can define a maximum width $W_1$ therebetween. In the second position, the minor springs 110 can be in the natural, un-constricted configuration, wherein the spring force of the minor springs 110 can bias the corresponding first and second legs 112,114 away from each other at the middle section 118 of the minor spring 110. In the un-constricted configuration, the first and second legs 112,114 can define a maximum width $W_2$ (shown in FIG. 3) therebetween that can be greater than the maximum width $W_1$ in the constricted configuration.

Referring to FIG. 2, as shown, in the present aspect, each of the spring constrictors 150 can substantially define an overall cube shape having an opening 252 formed therethrough. The opening 252 can define a substantially square cross-sectional shape, as shown, and can be configured to receive the first and second legs 112,114 of a corresponding minor spring 110 therethrough, and more specifically, the tail portions 117 of the first and second legs 112,114 therethrough. In other aspects, the overall shape of the spring constrictor 150 and the cross-sectional shape of the opening 252 formed therethrough can define any other suitable shape. To assemble each spring constrictor 150 with the corresponding minor spring 110, the first and second legs 112,114 can be pushed towards one another at the second end 120 of the minor spring 110, and the spring constrictor 150 can be slipped over the feet 122, with the feet 122 passing through the opening 252. For example, the first and second legs 112,114 can be pushed towards one another and the spring constrictor 150 can be mounted thereon manually in some aspects. In other aspects, the first and second legs 112,114 can be pushed together by a tool, a machine, or by any other suitable method for applying a force. The spring constrictor 150 can be slid along the first and second legs 112,114 to a position at or near a center of the middle section 118 of the minor spring 110, such that the spring constrictor 150 can force the first and second legs 112,114 towards each other at the middle section 118, as shown. The manual force, or other force, applied to the first and second legs 112,114 can be released, and the feet 122 can serve as a stop to prevent the spring constrictor 150 from sliding off the second end 120 of the minor spring 110.

A void 230 can extend through the stent spring 100, and fluid can be configured to flow therethrough. A center axis 232 can extend substantially through a center of the void 230, as shown. A release mechanism 260 can be positioned in the void 230, as shown. According to example aspects, each of the spring constrictors 150 can be operably connected to the release mechanism 260, such that generally axial movement of the release mechanism 260 relative to the stent spring 100 towards the second ends 120 of the minor springs 110 can result in generally axial movement of the spring constrictors 150 along the first and second legs 112,114 towards the second ends 120. In some aspects, the joint 119 along each of the first and second legs 112,114 can prohibit the spring constrictors 150 from moving axially towards the first end 116. According to some aspects, each of the spring constrictors 150 can comprise a connector, such as an ear 254, extending radially inward for operably connecting the spring constrictor 150 to the release mechanism 260, as shown. To move each spring constrictor 150 from the first position at or near a center the middle section 118 of the corresponding minor spring 110 to the second position proximate the second end 120 of the minor spring 110, the release mechanism 260 can be moved towards the second end 120 of the minor springs 110. The engagement of the release mechanism 260 with the connectors (e.g., the ears 254) of the spring constrictors 150 can pull the spring constrictors 150 along the first and second legs 112,114 towards the corresponding second ends 120.

In example aspects, the spring constrictors 150 can abut the corresponding feet 122 of the minor spring 110 in the second position and can be prevented from sliding off the minor spring 110 at the second end 120. Once the spring constrictors 150 are in the second position proximate the feet 122, the spring force of each of the minor springs 110 can bias the first and second legs 112,114 apart at the middle section 118 of the minor spring 110, moving each of the minor springs 110 from the constricted configuration to the un-constricted configuration. A diameter $D_1$ of the stent spring 100 can increase as the minor springs 110 move to the un-constricted configuration. In some aspects, as the diameter $D_1$ increases, the spring constrictors 150 can disengage and move radially outward from the release mechanism 260. The release mechanism 260 can then be removed, so that fluid can flow substantially uninterrupted through the void 230. In some other aspects, the spring constrictors 150 can be removed along with the release mechanism 260.

FIG. 3 illustrates an exploded view of the stent 300. The stent 300 can be configured to repair a damaged pipe 700 (shown in FIG. 7). As shown, the stent 300 can comprise the stent spring 100 and a seal 310. According to example aspects, the seal 310 can be formed as a hollow tubular sleeve 312 configured to receive the stent spring 100 therein. Example aspects of the seal 310 can comprise a flexible and resilient material, such as, for example, neoprene. The seal 310 can be flexible and resilient so that it can deform to match the profile of an inner wall 702 (shown in FIG. 7) of the pipe 700. In other aspects, the seal 310 can be formed from another synthetic rubber material such as EPDM rubber, natural rubber, foam, epoxy, silicone, a resin-soaked cloth, or any other suitable flexible material for providing a watertight seal with the pipe 700. In the present aspect, the seal 310 can be retained on the stent spring 100 by snugly wrapping around the stent spring 100 to create friction between the seal 310 and the stent spring 100. According to other example aspects, the seal 310 can be retained on the stent spring 100 by stitching, adhesives, ties, clips, or any other suitable fastener or combination of fasteners known in the art. According to example aspects, when the seal 310 is assembled with the stent spring 100, an inner surface 314 of the seal 310 can engage an outer surface 302 of the stent spring 100.

The minor springs 110 are illustrated in the un-constricted configuration in FIG. 3 with the spring constrictors 150 removed therefrom. As shown, the first and second legs 112,114 of each of the minor springs 110 can be biased outward by the spring force at the middle sections 118 of each minor spring 110. The increased distance between each corresponding pair of first and second legs 112,114 results in an increased diameter $D_1$ of the stent spring 100. As shown, in the un-constricted configuration, each of the corresponding pair of first and second legs 112,114 can also define the maximum width $W_2$ therebetween than can be greater than the maximum width $W_1$ in the constricted configuration. As the diameter $D_1$ of the stent spring 100 increases, the stent spring 100 can bias the seal 310 radially outward. As shown, as the first and second legs 112,114 are biased apart at the middle section 118 of the minor spring 110, the first and second legs 112,114 can remain connected together at the first end 116 of the minor spring 110. In addition, in the present aspect, the first and second legs 112,114 can be bent towards each other at or near the second end 120 of the minor spring 110, such that a distance $X_1$ between the first and second legs 112,114 at the second end 120 can be less than a distance $X_2$ between the tail portions 117 of the first and second legs 112,114 at the middle section 118.

Figure 4:
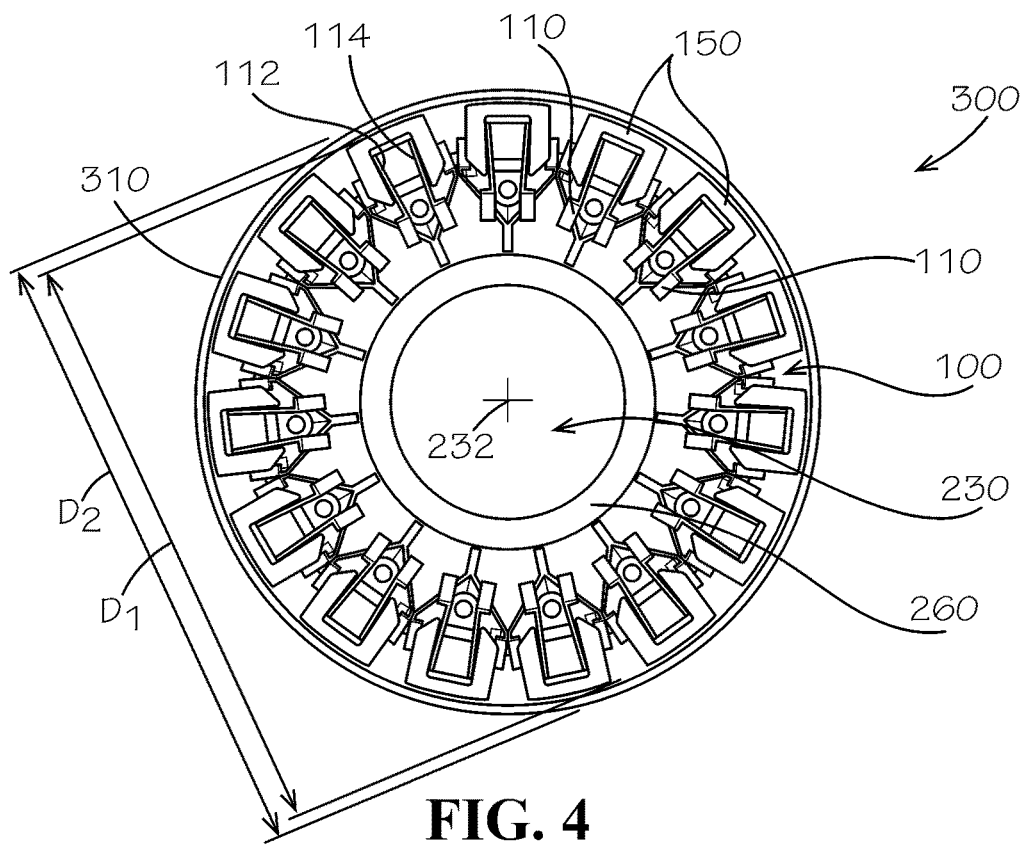
FIG. 4 is a front view of the stent of FIG. 3 in a compressed configuration.

FIG. 4 illustrates the stent 300 in a compressed configuration. In the compressed configuration, each of the minor springs 110 can be oriented in the constricted configuration, wherein the spring constrictors 150 can be in the first position and can bias the first and second legs 112,114 together at the middle section 118 (shown in FIG. 1), such that the diameter $D_1$ of the stent spring 100 can be reduced. The reduced diameter $D_1$ of the stent spring 100 can result in a reduced overall stent diameter $D_2$ of the stent 300, along with a reduced overall stent volume of the stent 300. Furthermore, when the stent 300 is oriented in the compressed configuration and the diameter $D_1$ of the stent spring 100 is reduced, the flexible seal 310 attached thereto can be drawn inward toward the center axis 232. As the seal 310 is drawn inward, in some aspects, the seal 310 may fold to define a plurality of inward folds extending generally radially inward relative to the center axis 232, outward folds extending generally radially outward in the, or may define a combination of inward folds and outward folds.

FIG. 5 illustrates the stent 300 in an expanded configuration. In the expanded configuration, each of the minor springs 110 can be oriented in the un-constricted configuration, wherein each of the spring constrictors 150 can be slid to the second end 120 of the corresponding minor spring 110 (i.e., the second position), and the first and second legs 112,114 can be biased apart at the middle section 118 (shown in FIG. 1) by the spring force, such that the diameter $D_1$ of the stent spring 100 can be increased. The increased diameter $D_1$ of the stent spring 100 can result in an increased overall stent diameter $D_2$, along with an increased overall stent volume. The seal 310 can be formed from a flexible and/or stretchable material, such that the seal 310 can be biased radially outward as the diameter $D_1$ of the stent spring 100 increases. FIG. 6 illustrates a perspective view of the stent spring 100 with each of minor springs 110 in the un-constricted configuration.

Figure 7:
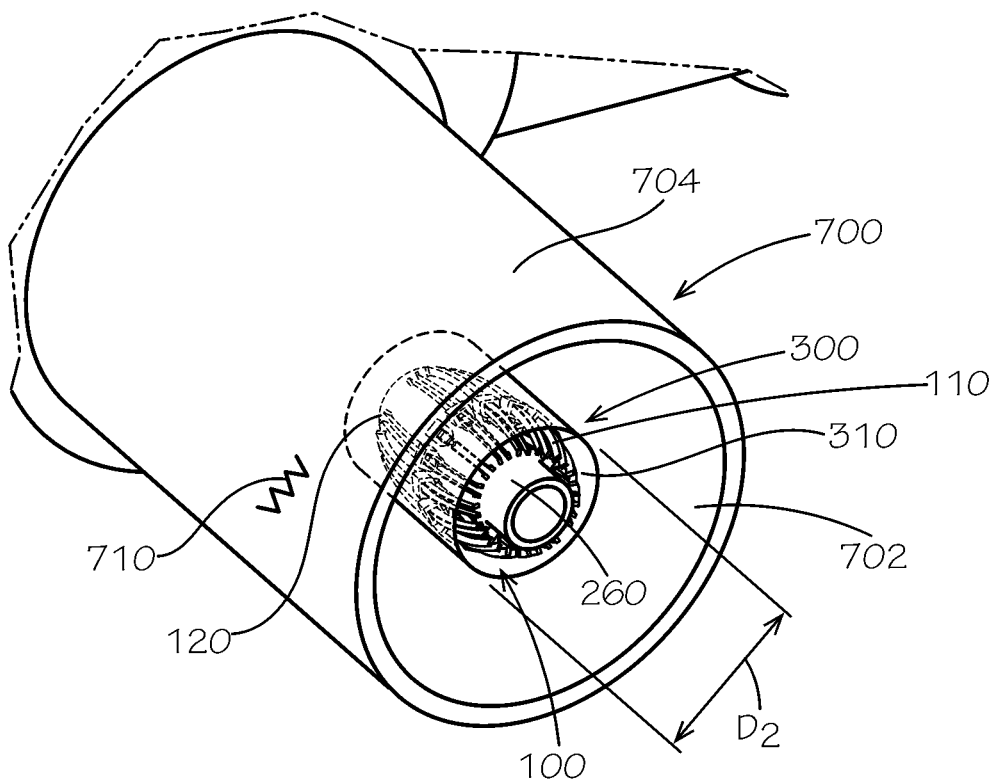
FIG. 7 is a top perspective view of the stent of FIG. 3 inserted into a pipe in the compressed configuration.
Figure 8:
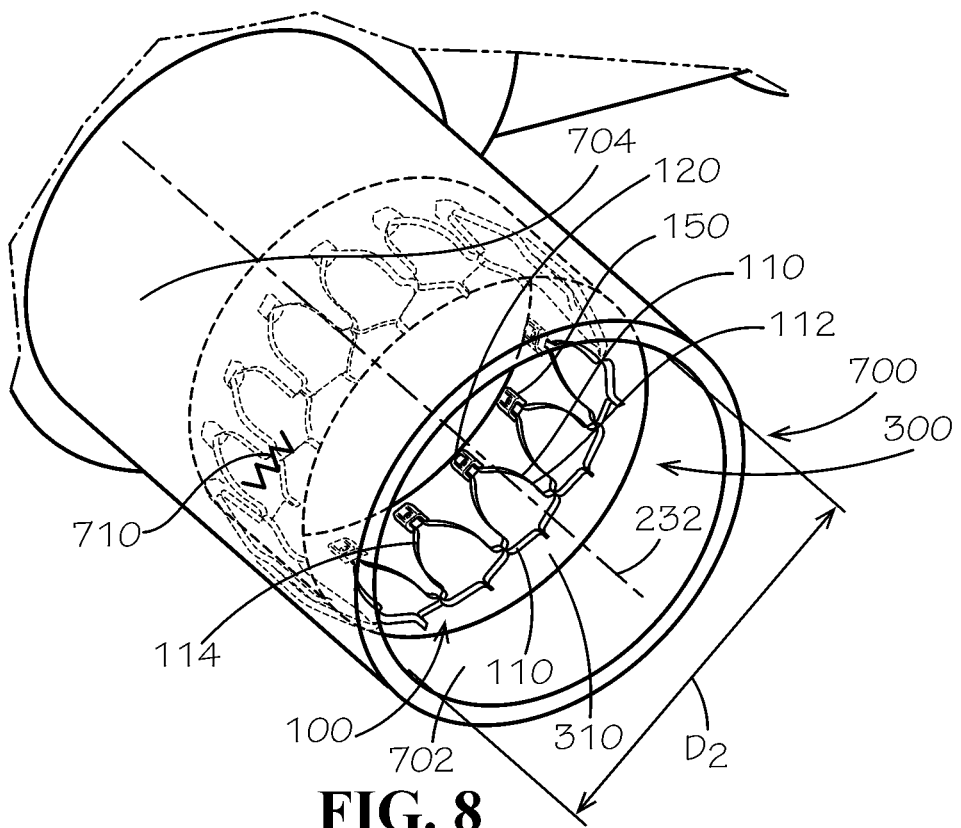
FIG. 8 is a top perspective view of the stent of FIG. 3 engaging the pipe of FIG. 7 in the expanded configuration.

FIG. 7 illustrates the stent 300 in the compressed configuration received within a damaged pipe 700. The pipe 700 can define an inner wall 702 and an outer wall 704, and a crack 710 or other damage can be present in the pipe 700. In the present aspect, the crack 710 can extend from the inner wall 702 of the pipe 700 to the outer wall 704, such that fluid within the pipe 700 can leak out of the pipe 700 through the crack 710. As shown, in the compressed configuration, the reduced overall diameter $D_2$ and decreased overall volume of the stent 300 can allow for easier insertion of the stent 300 into the pipe 700 or a pipeline and easier navigation of the stent 300 through the pipe 700 or pipeline. According to example aspects, the compressed stent 300 can be aligned with the crack 710 or other damage in the pipe 700 before the stent 300 is expanded to the expanded configuration. To configure the stent 300 in the expanded configuration, the release mechanism 260 can be moved axially relative to the stent 300 towards the second ends 120 of the minor springs 110, thus moving the spring constrictors 150 (shown in FIG. 1) from the first position to the second position.

FIG. 8 illustrates the stent 300 in the expanded configuration with the damaged pipe 700. Once the stent 300 is aligned with the crack 710 or other damage, the stent 300 can be expanded within the pipe 700, such that the seal 310 can engage the inner wall 702 of the pipe 700 where the crack 710 is present, in order to create a watertight seal between the stent 300 and the inner wall 702 to prevent leaking at the damage site. As described above, the stent 300 can be expanded by moving the release mechanism 260 (shown in FIG. 2) towards the second ends 120 of the minor springs 110, such that the spring constrictors 150 are moved along with the release mechanism 260 to the second end 120 of the corresponding minor spring 110. In the present aspect, each spring constrictor 150 can abut the corresponding feet 122 (shown in FIG. 1) of the corresponding minor spring 110, such that the feet 122 prevent the spring constrictor from detaching from the minor spring 110. The spring force of each minor spring 110 can then bias the corresponding first and second legs 112,114 to the un-constricted configuration, increasing the diameter $D_1$ (shown in FIG. 2) of the stent spring 100 and the overall stent diameter $D_2$. The stent spring 100 can define its largest diameter in the expanded configuration. The increased diameter $D_1$ of the stent spring 100 can bias the seal 310 radially outward relative to the central axis 232, such that the seal 310 can move towards and press against the inner wall 702 of the pipe 700. In some aspects, in the expanded configuration, the overall stent diameter $D_2$ can be slightly greater than a diameter of the inner wall 702 of the pipe 700, such that the stent 300 can apply a force in the radial direction against the inner wall 702 of the pipe 700.

As such, a method for repairing the pipe 700 can comprise orienting the minor springs 110 of the stent spring 100 in the constricted configuration in order to reduce the diameter $D_1$ (shown in FIG. 2) of the stent spring 100 and the overall stent diameter $D_2$ of the stent 300. The method can also comprise inserting the stent 300 into the pipe 700 and orienting the stent 300 proximate to the crack 710 or other damage in the pipe 700. The method can further comprise moving the minor springs 110 to the un-constricted configuration to increase the diameter $D_1$ of the stent spring 100 and the overall stent diameter $D_2$ of the stent 300. The method can then comprise engaging the inner wall 702 of the pipe 700 at the crack 710 (or other damage) with the seal 310 of the stent 300 to create a watertight seal between the stent 300 and the inner wall 702 of the pipe 700.

One should note that conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment.

It should be emphasized that the above-described embodiments are merely possible examples of implementations, merely set forth for a clear understanding of the principles of the present disclosure. Any process descriptions or blocks in flow diagrams should be understood as representing modules, segments, or portions of code which include one or more executable instructions for implementing specific logical functions or steps in the process, and alternate implementations are included in which functions may not be included or executed at all, may be executed out of order from that shown or discussed, including substantially concurrently or in reverse order, depending on the functionality involved, as would be understood by those reasonably skilled in the art of the present disclosure. Many variations and modifications may be made to the above-described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

That which is claimed is:

1. A stent for repairing a pipe comprising:
a stent spring comprising a plurality of minor springs connected in a series;
a spring constrictor engaged with each of the minor springs, each of the spring constrictors movable between a first position, wherein the stent is in a compressed configuration, and a second position, wherein the stent is in an expanded configuration; and
a seal configured to engage an inner wall of a pipe.

2. The stent of claim 1, wherein the seal defines a hollow, tubular sleeve formed from a flexible and resilient material.

3. The stent of claim 1, wherein:
each of the spring constrictor comprises a connector:
the stent further comprises a release mechanism connected to each of the connectors and configured for axial movement relative to the stent spring.

4. The stent of claim 1, wherein:
in the first position, each of the minor springs is in a constricted configuration and defines a first maximum width; and
in the second position, each of the minor springs is in an un-constricted configuration and defines a second maximum width that is greater than the first maximum width.

5. The stent of claim 1, wherein:
each of the minor springs defines a first end, a second end opposite the first end, and a middle section therebetween;
each of the spring constrictors is engaged with the middle section of the corresponding minor spring in the first position; and
each of the spring constrictors is engaged with the second end of the corresponding minor spring in the second position.

6. The stent of claim 5, wherein
each of the spring constrictors defines a first leg and a second leg;
the first leg and second leg of each minor spring are joined together at the corresponding first end;
the first leg and second leg of each minor spring are spaced apart at the corresponding middle section and second end;
each of the first leg and second leg define a head portion and a tail portion; and
each of the spring constrictors is mounted on the tail portions of the corresponding first leg and second leg.

7. A method for repairing a pipe comprising:
providing a stent comprising a stent spring and a seal, the stent spring comprising a plurality of minor springs;
orienting the minor springs in a constricted configuration to reduce a diameter of the stent, wherein orienting the minor springs in a constricted configuration comprises engaging each of the minor springs with a spring constrictor in a first position;
inserting the stent into a pipe;
orienting the minor spring in an un-constricted configuration to increase the diameter of the stent; and
engaging an inner wall of the pipe with the seal.

8. The method of claim 7, wherein engaging each of the minor springs with a spring constrictor in a first position comprises inserting a first leg and a second leg of each of the minor springs through an opening in a corresponding spring constrictor and sliding the spring constrictor along the first leg and second leg to the first position.

9. The method of claim 7, wherein orienting the minor spring in an un-constricted configuration comprises sliding each of the spring constrictors along the corresponding minor spring from the first position to a second position.

10. The method of claim 9, wherein sliding each of the spring constrictors along the corresponding minor spring from the first position to a second position comprises engaging a connector of each of the spring constrictors with a release mechanism and moving the release mechanism axially relative to the stent.

\* \* \* \* \*